United States Patent
Wang et al.

(10) Patent No.: US 7,994,378 B2
(45) Date of Patent: Aug. 9, 2011

(54) PROCESS OF BUTADIENE-1, 3 EXTRACTION

(76) Inventors: Minghua Wang, Beijing (CN); Duoshan Zhao, Beijing (CN); Meng Wang, Beijing (CN)

( * ) Notice: Subject to any disclaimer, the term of this patent is extended or adjusted under 35 U.S.C. 154(b) by 358 days.

(21) Appl. No.: 12/397,939

(22) Filed: Mar. 4, 2009

(65) Prior Publication Data
US 2009/0234172 A1    Sep. 17, 2009

(30) Foreign Application Priority Data
Mar. 12, 2008    (CN) .......................... 2008 1 0101812

(51) Int. Cl.
*C07C 7/08*    (2006.01)
(52) U.S. Cl. ......... 585/810; 585/833; 585/809; 585/807
(58) Field of Classification Search .................. None
See application file for complete search history.

(56) References Cited

U.S. PATENT DOCUMENTS

| | | | |
|---|---|---|---|
| 3,484,221 A * | 12/1969 | Clay ............................ | 48/197 R |
| 4,054,613 A * | 10/1977 | Haskell et al. ................ | 585/633 |
| 4,091,046 A * | 5/1978 | Dixon ........................... | 585/315 |
| 4,134,795 A * | 1/1979 | Howat, III ...................... | 203/53 |
| 6,395,952 B1 * | 5/2002 | Barchas ......................... | 585/833 |
| 7,348,466 B2 * | 3/2008 | Bridges et al. ................ | 585/809 |

* cited by examiner

*Primary Examiner* — Tam M Nguyen
(74) *Attorney, Agent, or Firm* — J.C. Patents

(57) ABSTRACT

This invention presents a process of butadiene-1,3 extraction. The process consists of the procedure of 1st extractive fractionation, 2nd extractive fractionation, distillation and alkyne fractionation. This invention can improve the yield and capacity of butadiene extraction unit by adding an alkyne fractionator to the existing butadiene extraction unit and appropriately adjusting the process condition of 1st and 2nd extractive fractionators. This invention can decrease the energy and material consumption per unit of butadiene-1,3, which greatly improved the economic profit. The investment on various scales of butadiene extraction units for adding alkyne fractionator is almost same. Further more, the profit is in direct proportion with the scale of a plant and output is in several to some dozens of folds to investment. After the implementation of this invention, the discharge of vinyl acetylene offgas can be reduced by around 3400 tons per year, which mitigate the pollution on environment and save energy. The effect of energy saving and emission reduction is remarkable.

2 Claims, 2 Drawing Sheets

PROCESS OF BUTADIENE-1, 3 EXTRACTION

CROSS-REFERENCE TO RELATED APPLICATION

This application claims the priority benefits of China application No. 200810101812.X filed on Mar. 12, 2008, the contents of which are hereby incorporated by reference in its entirety.

FIELD OF THE INVENTION

This invention presents a process of butadiene-1,3 ($CH_2$=CH—CH=$CH_2$) extraction. It takes C4 distillate of ethylene plant as feedstock and adds an alkyne fractionator to the existing butadiene extraction unit to improve the yield. By utilizing the alkyne fractionator, the throughput of butadiene extraction unit can be boosted if adjusting the process condition of $1^{st}$ and $2^{nd}$ extractive fractionators.

TECHNICAL BACKGROUND

Butadiene-1,3 is an important petrochemical organic raw material, a monomer of synthetic rubber and an uppermost component in C4 distillate as well. In raw materials of petrochemical olefin, it ranks only next to ethylene and propylene. It can pose the reaction of substitution, addition, cyclization, and polymerization due to conjugated double bond contained in its molecule, which enable it to be widely applied to the area of synthetic rubber and organic composition. It can be fabricated to various rubber products such as (cis-butadiene rubber) BR, styrene butadiene rubber (SBR), nitrile butadiene rubber, styrene-butadiene-styrene (SBS), acrylonitrile-butadiene-styrene (ABS) resin. In addition, it can not only produce organic petrochemical products like adiponitrile, hexamethylene diamine, nylon 66, 1,4-butyl glycol, but also adhesives, gasoline additives, etc. The utilization is highly broad.

The source of butadiene-1,3 in industry is mainly from two means. One is to be obtained by dehydrogenation and extraction of C4 distillate from refinery. Currently, only a few countries, which possess abundant resource of butane and butylene, are making use of it. The throughput accounts for about 8%. The other one is to be attained by extraction of mixed C4 distillate co-produced from ethylene cracker. This method is in the ascendant in economy due to low cost and is the main source of butadiene-1,3 globally at present. The output accounts for around 92%.

The butadiene-1,3 separation process fed by mixed C4 distillate co-produced from ethylene cracker, butadiene-1,3 extraction process, as taking different solvent, is classified to three categories, acetonitrile (ACN) process, dimethyl formamide (DMF) process and N-methyl pyrrolidone (NMP) process.

The yield of butadiene-1,3 extraction of acetonitrile (ACN) process, dimethyl formamide (DMF) process and N-methyl pyrrolidone (NMP) process is about 97%. The rest 3% of butadiene-1,3, except butadiene dimer, is carried off by butane&butalene distillate, vinyl acetylene offgas, methyl acetylene offgas and waste C4C5 discharged from $2^{nd}$ extractive fractionator bottom separately. In view of the feasibility of construction investment and routine operation cost of butadiene extraction unit, in the process of plant design and practical production, the content specification of butane&butalene distillate, vinyl acetylene offgas, methyl acetylene offgas and waste C4C5 discharged from $2^{nd}$ extractive fractionator bottom are assured. The loss of butadiene-1,3 in vinyl acetylene offgas, methyl acetylene offgas is in relation to the content of vinyl acetylene and methyl acetylene in C4 feed. The higher content of vinyl acetylene and methyl acetylene is in C4 feed, the more butadiene-1,3 is losing. Because the loss of butadiene-1,3 caused by vinyl acetylene offgas accounts for large proportion in total, in order to avoid losing butadiene-1,3, measure taken in most of technology is to improve vinyl acetylene content in vinyl acetylene offgas to reduce butadiene-1,3 content. Meanwhile, for the purpose of safety, butane&butylene distillate is added for dilution. Though the measure works to some extent, there is no big change on it. The loss of butadiene-1,3 is still considerable.

Along with the development of auto industry, the demand for rubber products like tires is constantly increased. The demand for butadiene-1,3, as a main raw material of rubber production, is progressive accordingly. Therefore, many manufactories commit themselves to challenge butadiene extraction unit to get more and more production load, even produce with over-load at the cost of increasing loss of butadiene-1,3. Even so, many manufactories, whose development is in the restriction of production, invest to build new butadiene extraction units and the newly-built butadiene extraction unit tends to large scale. Some manufactories own two or three butadiene extraction units.

In consideration of increasing demand of butadiene-1,3, one approach is to build new butadiene extraction unit. However, it will take large cost and long period. There are around 20 sets of butadiene extraction units in China and about 100 sets across the world. Therefore, updating and tapping the potential of the existing butadiene unit, improving the yield and capacity of it is another option to expand output of butadiene-1,3. It is an effective route with low investment and fast effect as well.

SUMMARY OF THE INVENTION

The purpose of this invention is to present a process of butadiene-1,3 extraction. The process can improve the yield and capacity of butadiene extraction unit by adding an alkyne fractionator to the existing butadiene extraction unit and appropriately adjusting the process condition of $1^{st}$ and $2^{nd}$ extractive fractionators.

The objective of this invention is realized by the following technical proposal: a process of butadiene-1,3 extraction, including the procedure of $1^{st}$ extractive fractionation, $2^{nd}$ extractive fractionation, distillation and alkyne fractionation. The steps of butadiene-1,3 extraction process mentioned above are listed as below:

A. $1^{st}$ extractive fractionation procedure: C4 material is fed to the middle of $1^{st}$ extractive fractionator. Solvent is introduced from the top of it. By extractive fractionating, butane&butylene is separated from the top of the column. Butadiene-1,3, trans-butylene-2, cis-butylene-2, butadiene-1,2, butyne-1, vinyl acetylene and solvent are discharged from the bottom of the column to $1^{st}$ stripper. After separation, butadiene-1,3, trans-butylene-2, cis-butylene-2, butadiene-1, 2, butyne-1, vinyl acetylene get out from the top of $1^{st}$ stripper and solvent is discharged from the bottom of it.

B. $2^{nd}$ extractive fractionation procedure: Butadiene-1,3, trans-butylene-2, cis-butylene-2, butadiene-1,2, butyne-1, vinyl acetylene discharged from the top of $1^{st}$ stripper are pressurized by compressor, and then enter to the bottom of $2^{nd}$ extractive fractionator. Solvent is introduced from the top of $2^{nd}$ extractive fractionator. By extractive fractionation, crude butadiene comes out from the top of the column and liquid in the column is discharged from the bottom to butadiene recovery column. After separation, butadiene-1,3 discharged from the top of the butadiene recovery column is fed to compressor and liquid of the column gets out from the bottom to $2^{nd}$ stripper. The vinyl acetylene offgas is discharged from the top of $2^{nd}$ stripper after separation and solvent comes out from the bottom of the column.

C. Distillation procedure: The crude butadiene from $2^{nd}$ extractive fractionator goes to the top of $1^{st}$ distillation column. By separation, methyl acetylene offgas is discharged from the top of it. The bottom is sent to the upper of $2^{nd}$ distillation column for separation. Then, butadiene-1,3 is drawn from the top of $2^{nd}$ distillation column and bottom waste C4C5 is discharged to vaporizer to remove inhibitor, and then enters to the top of $2^{nd}$ stripper for diluting vinyl acetylene offgas.

D. Alkyne fractionation procedure: butane&butylene separated by procedure A partially go to the top of alkyne fractionator. Vinyl acetylene offgas separated from procedure B enter the bottom of alkyne fractionator and methyl acetylene offgas from procedure C is put in the top of alkyne fractionator. By re-separating, butadiene-1,3 is side-drawn from the middle of alkyne fractionator and returns $1^{st}$ extractive fractionator through feed vaporizer. Methyl acetylene is vent from the top of alkyne fractionator and vinyl acetylene is discharged from the bottom of it.

The butadiene-1,3 extraction process is to drop solvent ratio and reflux ratio of $1^{st}$ extractive fractionator in procedure A to have the content of trans-butylene-2 separated from the bottom of $1^{st}$ extractive fractionator around 0.1-0.15% and cis-butylene-2 about 3.0-3.5%. In procedure C, the discharge amount of waste C4C5 from bottom of $2^{nd}$ extractive fractionator is increased to have 10-15% content of butadiene-1,3.

In comparison with prior art, this invention has the following advantages:

1. The contents discharged by current butadiene extraction process are listed as follows: methyl acetylene and butadiene-1,3 in methyl acetylene offgas are about 35% and 65% respectively, vinyl acetylene and butadiene-1,3 in vinyl acetylene offgas are around 50% and 30% separately and butadiene-1,3 in waste C4C5 is approximately 5%. The methyl acetylene offgas, vinyl acetylene offgas and waste C4C5 are separated by the alkyne fractionator in this invention. The butadiene-1,3 content in methyl acetylene offgas vent from the top of alkyne fractionator drops to around 10%. Butadiene-1,3 in vinyl acetylene remaining liquid discharged from the bottom of alkyne fractionator decline to about 1%. By removing inhibitor, waste C4C5 is utilized for vinyl acetylene offgas dilution, while prior art uses butane&butylene to dilute vinyl acetylene offgas. Most of butadiene-1,3 in waste C4C5 can be recovered. By re-separating in alkyne fractionator, over 85% of the total content of butadiene-1,3 in methyl acetylene offgas, vinyl acetylene offgas and waste C4C5 can be recovered and the yield of butadiene-1,3 can be improved by 1-2%.

2. This invention is to re-separate methyl acetylene offgas, vinyl acetylene offgas and waste C4C5 by adding alkyne fractionator, appropriately drop solvent ratio and reflux ration in $1^{st}$ extractive fractionator, relax quality control index of cis-butylene-2 and trans-butylene-2 in $1^{st}$ extractive fractionator, properly increase liquid discharge amount of $2^{nd}$ extractive fractionator, broaden butadiene quality control index in $2^{nd}$ extractive fractionator to boost C4 feed and to improve the plant capacity by about 10%.

3. Current butadiene extraction unit has the butadiene-1,3 production scale ranging from the minimum 20 kilotons to maximum 540 kilotons. Being illustrated by a 100 kilotons butadiene-1,3 output of butadiene extraction unit, the throughput of butadiene-1,3 can be increased by 1000 tons if the yield of butadiene-1,3 is improved by 1% and in the event of 2% butadiene-1,3 increase, 2000 tons of butadiene-1,3 output can be achieved and the energy and material consumption per unit of butadiene-1,3 is decreased, which greatly improved the economic profit. The investment on various scales of butadiene extraction units is almost same. Furthermore, the profit is in direct proportion with the scale of a plant and output is in several to some dozens of folds to investment.

4. In order to cut down the loss of butadiene-1,3, the measure taken by prior art is to increase the vinyl acetylene content in vinyl acetylene offgas vent from the top of $2^{nd}$ stripper to decrease butadiene-1,3 content. Meanwhile, in the interest of security, butane&butylene is fed for dilution. After diluting, vinyl acetylene concentration in vinyl acetylene offgas (with concentration below 50% and partial pressure under 0.075 Mpa) is in safe operational status. No matter vinyl acetylene offgas being diluted by butane&butylene or not, most of the discharged vinyl acetylene offgas is channeled to flare. For some reusable matters, it requires investment for equipment and operational cost and the effect isn't attractive. This invention substitutes waste C4C5 without inhibitor for butane&butylene to dilute vinyl acetylene offgas. The dilution amount of C4C5 is greater than that of butane&butylene. Therefore, vinyl acetylene resid discharged from the bottom of alkyne fractionator is in line with safety requirement and can be used as fuel. For the process of butadiene-1,3 extraction with feed of mixed C4 distillate co-produced by ethylene cracker, C4 feed contains 0.5-1.0% of vinyl acetylene with average of about 0.8%. A butadiene extraction unit with 100 kta of butadiene-1,3 production rate is still cited as an example. After the implementation of this invention, the discharge of vinyl acetylene offgas can be reduced by around 3400 tons per year, which decrease the environmental pollution, save energy. The effect of energy saving and emission reduction is remarkable.

EMBODIMENTS

Expatiation on this invention in some embodiments is as follows.

Normally, C4 distillate from ethylene cracker consists of water, propane, propyne(methyl acetylene), iso-butane, n-butane, iso-butylene, n-butylene, trans-butylene-2, cis-butylene-2, butylene-1,3, butylene-1,2, butyne-1(ethyl acetylene), vinyl acetylene, di-methyl-butylene-1, tri-methyl-butylene-1 and C5. After being separated by butadiene extraction unit, final product, butadiene-1,3, is obtained and all the others are removed. The quality indexes of butadiene-1,3 are listed as follows: purity≧99.5%, vinyl acetylene and butyne-1(ethyl acetylene)≦20 ppm, water≦20 ppm.

There are three process routes for the butadiene-1,3(Butadiene,$CH_2$=CH—CH=$CH_2$) extraction fed by C4 distillate co-produced from ethylene cracker, i.e. CAN process, DMF process and NMP process. Despite of three different processes, they have same function, separated components, target product and impurities to remove, including similar composition of methyl acetylene offgas, vinyl acetylene offgas and waste C4C5 and their destination. In a concise, only DMF process is given as an example for expatiation on this invention.

Example 1

Figure 1:
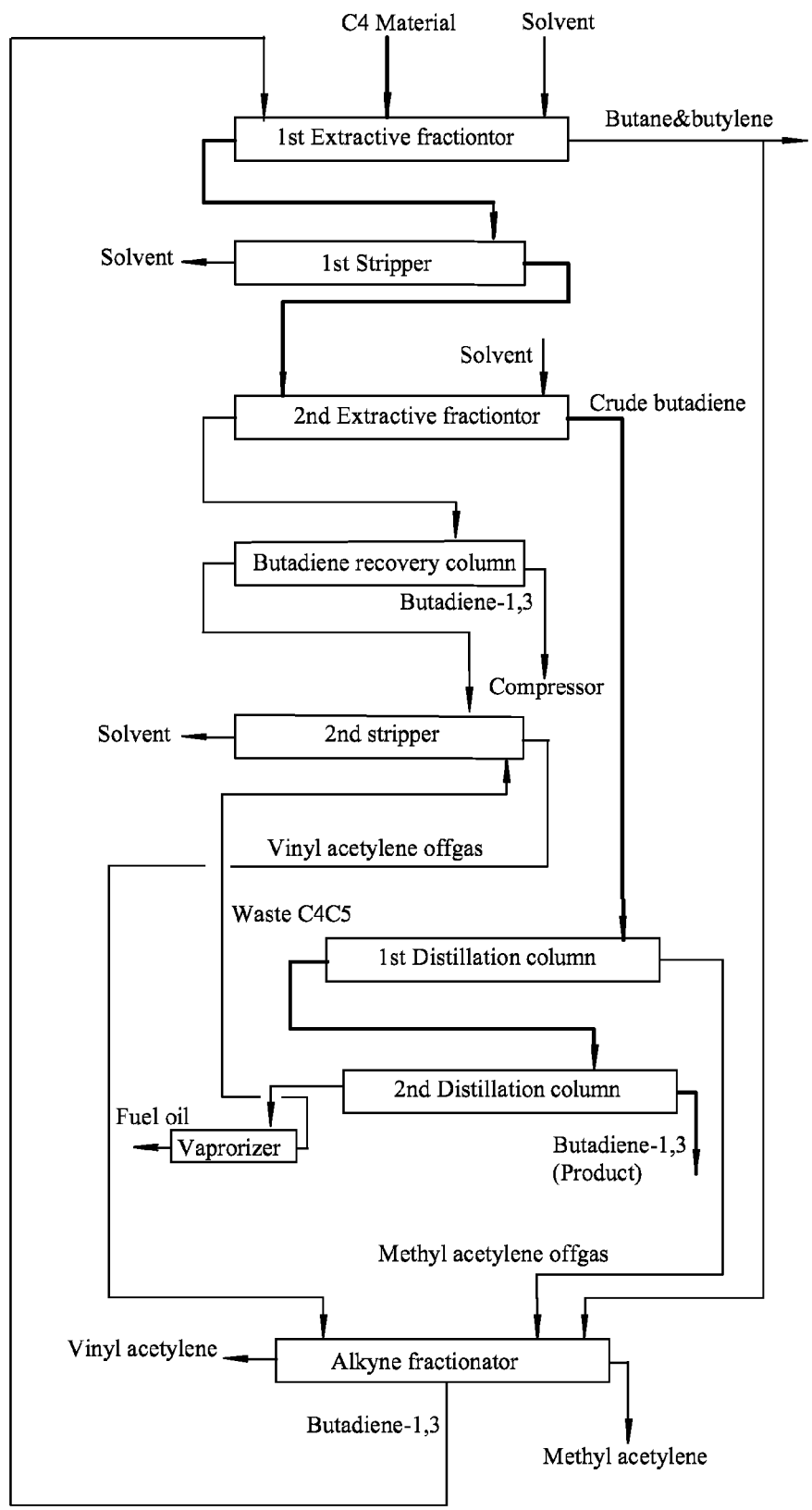
FIG. 1 A process of butadiene-1,3 extraction flow diagram of this invention.
Figure 2:
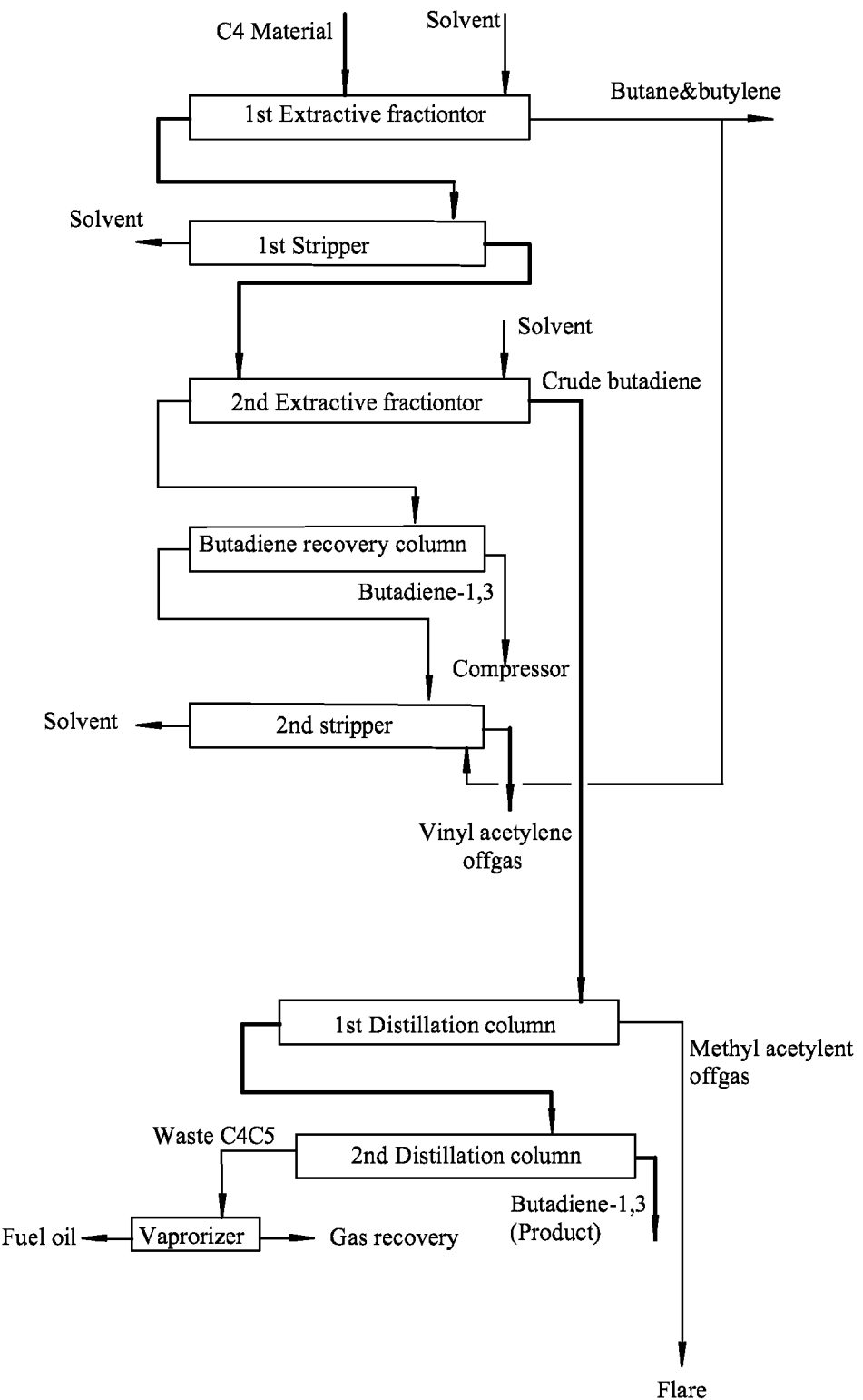
FIG. 2 A process of butadiene-1,3 extraction flow diagram of prior art.

See FIGS. 1 and 2 a process of butadiene-1,3 extraction, including the procedure of extractive fractionation, distillation and alkyne fractionation. The steps of butadiene-1,3 extraction process mentioned above are listed as below:

A. $1^{st}$ extractive fractionation procedure: C4 material is fed to the middle of $1^{st}$ extractive fractionator. Solvent is introduced from the top of it. By extractive fractionating, butane&butylene is separated from the top of the column. Butadiene-1,3, trans-butylene-2, cis-butylene-2, butadiene-1,2, butyne-1, vinyl acetylene (all the components except butadiene-1,3 are small quantity) and solvent are discharged from the bottom of the column to $1^{st}$ stripper. After separation, butadiene-1,3, trans-butylene-2, cis-butylene-2, butadiene-1,2, butyne-1, vinyl acetylene get out from the top of $1^{st}$ stripper to $2^{nd}$ extractive fractionator and solvent is discharged from the bottom of it.

Under the action of solvent, all the components whose relative volatility is greater than butadiene-1,3 by 1.0 should be removed by this procedure through $1^{st}$ extractive fractionator. Whereas, butadiene-1,3 and the components whose relative volatility is lower than butadiene-1,3 by 1.0 are in company with solvent to be discharged from the bottom of $1^{st}$ extractive fractionator to enter $1^{st}$ stripper.

The butadiene-1,3 in butane&butylene is specified as ≦0.3%. The trans-butylene-2 in the component discharged from the bottom of $1^{st}$ extractive fractionator whose relative volatility is lower than butadiene-1,3 by 1.0 is controlled at ≦0.05%. Cis-butylene-2 is specified at ≦2.5%. The pressure of $1^{st}$ extractive fractionator is 0.39 Mpa and the temperatures of top and bottom of it are 42° C. and 130° C. respectively. The top pressure of $1^{st}$ stripper is 0.015 Mpa and the bottom temperature of it is 163° C.

B. $2^{nd}$ extractive fractionation procedure: Butadiene-1,3, trans-butylene-2, cis-butylene-2, butadiene-1,2, butyne-1, vinyl acetylene discharged from the top of $1^{st}$ stripper are pressurized by compressor to the bottom of $2^{nd}$ extractive fractionator. Solvent is introduced from the top of $2^{nd}$ extractive fractionator. By extractive fractionation, crude butadiene (butadiene-1,3 and small quantity of thans-butylene-2, cis-butylene-2, butadiene-1,2 and methyl acetylene) comes out from the top of $2^{nd}$ extractive fractionator to $1^{st}$ fractionator (in the action of solvent, all the components whose relative volatility is lower than butadiene-1,3 by 1.0 should be removed by this procedure through $2^{nd}$ extractive fractionator such as vinyl acetylene, ethyl acetylene, butadiene-1,2 and C5 etc.) and liquid in the column is discharged to butadiene recovery column. After separation, butadiene-1,3 discharged from the top of the butadiene recovery column is pressurized by compressor to be recycled to $1^{st}$ and $2^{nd}$ extractive fractionators. The bottom from butadiene recovery column is sent to $2^{nd}$ stripper. By separating, the vinyl acetylene offgas is discharged from the top of $2^{nd}$ stripper and solvent comes out from the bottom of the column.

The solvent drained from $1^{st}$ and $2^{nd}$ strippers can be directly recycled to $1^{st}$ and $2^{nd}$ extractive fractionators. If the solvent contains too many impurities, such as water, butadiene dimer, tar etc, then a certain proportion of solvent (for instance, 1%) is required to be treated and return $1^{st}$ and $2^{nd}$ extractive fractionators for recycle.

Prior art makes use of solvent recovery column and solvent regeneration column to remove water, butadiene dimer, tar in solvent to ensure solvent quality fed to extractive fractionator. Solvent recovery column is to remove the matters whose boiling point is lower than it such as water and butadiene dimer, while solvent regeneration column is to eliminate the substance whose boiling point is higher than it, such as tar, etc.

The vinyl acetylene in crude butadiene separated from the top of $2^{nd}$ extractive fractionator is specified at ≦5 ppm. Vinyl acetylene offgas contains quite a number of butadiene-1,3 (about 30%). For cutting down the loss of butadiene-1,3, vinyl acetylene in vinyl acetylene offgas can be increased. For safe consideration, prior art typically connects butane&butylene to the top of $2^{nd}$ stripper for vinyl acetylene dilution. This embodiment injects waste C4C5 without inhibitor to dilute the vinyl acetylene offgas at the top of $2^{nd}$ stripper to substitute prior art by injecting butane&butylene for vinyl acetylene offgas dilution.

The parameters of $2^{nd}$ extractive fractionator are listed as follows: top pressure 0.35 Mpa, top temperature 41° C., bottom temperature 125-135° C. The parameters of butadiene recovery column are that top pressure 0.015 Mpa, bottom temperature 120-145° C. The top pressure of $2^{nd}$ stripper is 0.01 Mpa and top and bottom temperatures are 100-130° C. and 163° C. respectively.

C. Distillation procedure: The crude butadiene from $2^{nd}$ extractive fractionator goes to the top of $1^{st}$ distillation column. By separation, methyl acetylene offgas is discharged from the top of it. The bottom is sent to the upper of $2^{nd}$ distillation column for separation. Then, butadiene-1,3 is drawn from the top of $2^{nd}$ distillation column and bottom waste C4C5 is discharged to vaporizer to remove inhibitor, and then enters to the top of $2^{nd}$ stripper for diluting vinyl acetylene offgas.

A small quantity of impurities being unable to get rid of by $1^{st}$ and $2^{nd}$ extractive fractionation procedure (viz. the component whose relative volatility is close to that of butadiene-1,3 by 1.0) is removed by this procedure. Methyl acetylene goes to the upper of alkyne fractionator. Methyl acetylene in methyl acetylene offgas is 35% and butadiene-1,3 is 65%. The quality specifications of butadiene-1,3 products are listed as follows: butadiene-1,3≧99.5%, vinyl acetylene and butyne-1(ethyl acetylene)≦20 ppm, water≦20 ppm.

Waste C4C5 discharged by $2^{nd}$ distillation column enters to waste C4C5 vaporizer to remove inhibitor. Waste C4C5 without inhibitor (gas phase) goes to the top of $2^{nd}$ stripper (in lieu of prior art by using butane&butylene) to dilute vinyl acetylene offgas. The resid is to be used as fuel oil. Butadiene-1,3 in waste C4C5 gas is specified as ≦5%.

The top pressure of $1^{st}$ distillation column is 0.42 Mpa and the top and bottom temperatures are 41.8° C. and 50° C. respectively. The top pressure of $2^{nd}$ distillation column is 0.4 Mpa and top and bottom temperatures are 44.8° C. and 62° C. individually.

D. Alkyne fractionation procedure: butane&butylene separated by procedure A partially (with the same amount of methyl acetylene offgas) go to the top of alkyne fractionator. Vinyl acetylene offgas separated from procedure B (waste C4C5 diluted vinyl acetylene offgas without inhibitor) enter the bottom of alkyne fractionator and methyl acetylene offgas from procedure C is put in the top of alkyne fractionator. By re-separating, butadiene-1,3 is side-drawn from the middle of alkyne fractionator and returns $1^{st}$ extractive fractionator through feed vaporizer. Methyl acetylene is vent from the top of alkyne fractionator and vinyl acetylene is discharged from the bottom of it.

In this embodiment, based on the material composition and separation requirement, butane&butylene, methyl acetylene offgas and vinyl acetylene offgas are fed by three different inlets to alkyne fractionator.

Butane&butylene, methyl acetylene offgas and vinyl acetylene offgas are re-separated in alkyne fractionator. Methyl acetylene and butadiene-1,3 in methyl acetylene offgas feedstock are about 35% and 65% respectively; vinyl acetylene and butadiene-1,3 in vinyl acetylene offgas are around 50% and 30% separately. By re-separation of alkyne fractionator, the composition of methyl acetylene gas and vinyl acetylene resid has been reformed. Butadiene-1,3 in methyl acetylene offgas is replaced by butane&butylene and butadiene-1,3 in vinyl acetylene offgas is substituted by cis-butylene-2 (in waste C4C5). Waste C4C5 gas in company with vinyl acetylene offgas as its dilute gas enters to alkyne fractionator for re-separation. Most of butadiene-1,3 is recovered. By calculation, after being re-separated by alkyne fractionator, the butadiene-1,3 in methyl acetylene offgas vent from the top of alkyne fractionator is around 10% and to be sent to flare (hard to recovery by regular method). Butadiene-1,3 in vinyl acetylene remaining resid discharged from the bottom of alkyne fractionator decline to about 1% for the use of fuel. Butadiene-1,3 side-drawn from the middle of alkyne fractionator goes through feed vaporizer to $1^{st}$ extractive fractionator. Butadiene-1,3 from side-draw accounts for over 85% of the total content of butadiene-1,3 fed to alkyne fractionator.

The top pressure of alkyne fractionator is about 0.4 Mpa and top temperature of it is around 40° C. The alkyne fractionator described in this embodiment has high-efficient structured gauze packing in it.

Example 2

In order to further boost the throughput of butadiene-1,3 on the basis of improved yield, based on Example 1, this embodiment appropriately adjusted the process conditions.

A process of butadiene-1,3 extraction, including the procedure of $1^{st}$ extractive fractionation, $2^{nd}$ extractive fractionation, distillation and alkyne fractionation. The steps of butadiene-1,3 extraction process mentioned above are listed as below:

A. $1^{st}$ extractive fractionation procedure: C4 material is fed to the middle of $1^{st}$ extractive fractionator. Solvent is introduced from the top of it. By extractive fractionating, butane&butylene is separated from the top of the column. Butadiene-1,3, trans-butylene-2, cis-butylene-2, butadiene-1,2, butyne-1, vinyl acetylene and solvent are discharged from the bottom of the column to $1^{st}$ stripper. After separation, butadiene-1,3, trans-butylene-2, cis-butylene-2, butadiene-1,2, butyne-1, vinyl acetylene get out from the top of $1^{st}$ stripper to $2^{nd}$ extractive fractionator and solvent is discharged from the bottom of it.

In this step of the embodiment, solvent ratio and reflux ratio of $1^{st}$ extractive fractionator are properly decreased to have 0.1-0.15% of trans-butylene-2 and 3.0-3.5% of cis-butylene-2 discharged from the bottom of $1^{st}$ extractive fractionator.

B. $2^{nd}$ extractive fractionation procedure: Butadiene-1,3, trans-butylene-2, cis-butylene-2, butadiene-1,2, butyne-1, vinyl acetylene discharged from the top of $1^{st}$ stripper are pressurized by compressor, and then enter to the bottom of $2^{nd}$ extractive fractionator. Solvent is introduced from the top of $2^{nd}$ extractive fractionator. By extractive fractionation, crude butadiene (butadiene-1,3 and small amount of trans-butylene-2, cis-butylene-2, butadiene-1,2 and methyl acetylene) comes out from the top to $1^{st}$ distillation column (with the function of solvent, all the components whose relative volatility is less than that of butadiene-1,3 by 1.0 are removed by $2^{nd}$ extractive fractionator in this procedure such as vinyl acetylene, ethyl acetylene, butadiene-1,2 and C5). The liquid in the column is discharged from the bottom to butadiene recovery column. After separation, butadiene-1,3 discharged from the top of the butadiene recovery column is pressurized by compressor and sent to $1^{st}$ and $2^{nd}$ extractive fractionators. The liquid of the column gets out from the bottom to $2^{nd}$ stripper. The vinyl acetylene offgas is discharged from the top of $2^{nd}$ stripper after separation and solvent comes out from the bottom of the column.

C. Distillation procedure: The crude butadiene from $2^{nd}$ extractive fractionator goes to the top of $1^{st}$ distillation column. By separation, methyl acetylene offgas is discharged from the top of it. The bottom is sent to the upper of $2^{nd}$ distillation column for separation. Then, butadiene-1,3 is drawn from the top of $2^{nd}$ distillation column and bottom waste C4C5 is discharged to vaporizer to remove inhibitor, and then enters to the top of $2^{nd}$ stripper for diluting vinyl acetylene offgas.

This procedure in the embodiment properly increases the discharge quantity of waste C4C5 in $2^{nd}$ distillation column to have 10-15% of butadiene-1,3 content.

D. Alkyne fractionation procedure: butane&butylene separated by procedure A partially (with the same amount of methyl acetylene offgas) go to the top of alkyne fractionator. Vinyl acetylene offgas separated from procedure B (waste C4C5 diluted vinyl acetylene offgas without inhibitor) enter the bottom of alkyne fractionator and methyl acetylene offgas from procedure C is put in the top of alkyne fractionator. By re-separating, butadiene-1,3 is side-drawn from the middle of alkyne fractionator and returns $1^{st}$ extractive fractionator through feed vaporizer. Methyl acetylene is vent from the top of alkyne fractionator and vinyl acetylene is discharged from the bottom of it.

After the completion of construction and installation of alkyne fractionator system and being ready for start-up, at the status of steady operation of the existing butadiene extraction unit and well-preparation, alkyne fractionator is shifted for use. The overall unit including alkyne fractionator should be gradually tuned to steady state after alkyne fractionator is put into operation. When the whole unit including alkyne fractionator is in smooth operation, the solvent ratio and reflux ratio are properly decreased and trans-butylene-2 and cis-butylene-2 in the bottom of $1^{st}$ extractive fractionator are moderately broadened. In Embodiment 1, the control index of trans butylene-2 in $1^{st}$ extractive fractionator is 0.05% and cis-butylene-2 is 2.5%. In Embodiment 2, the control index of trans-butylene-2 can be properly broadened to 0.1-0.15% and cis-butylene-2 is loosened to 3.0-3.5%. It increases the discharge of $2^{nd}$ distillation column bottom (waste C4C5) and broadens the index of butadiene-1,3 in $2^{nd}$ distillation bottom. The control index of butadiene-1,3 in $2^{nd}$ distillation bottom is widened from 5% in Embodiment 1 to 10-15% in Embodiment 2. By the quality analysis result of $1^{st}$ distillation bottom, it is confirmed that 0.1-0.15% of trans-butylene-2 in bottom and 3.0-3.5% of cis-butylene-2 are the proper solvent ratio and reflux ratio of $1^{st}$ extractive fractionator. Based on the quality analysis result of $2^{nd}$ distillation bottom, 10-15% of butadiene-1,3 in bottom is confirmed as the proper bottom (waste C4C5) discharge amount of $2^{nd}$ distillation column. The process conditions of $1^{st}$ extractive fractionator and $2^{nd}$ distillation column are adjusted again after alkyne fractionator is in service. In new extraction process condition, when the whole unit including alkyne fractionator is in smooth operation, if C4 feed rate improved, the capacity of the unit can be increased by 10%. The operation condition of boosting load is similar as that of existing butadiene-1,3 extraction unit.

In integral consideration of Embodiment 1 and Embodiment 2, the advantages of this invention are as follows: 1. yield improvement, 2. energy saving, 3. capacity increase. Prior to boosting load, if process conditions of $1^{st}$ extractive fractionator and $2^{nd}$ distillation column are not adjusted, it can not save energy and relax throughput. If the process conditions are adjusted before increasing load, it not only can improve yield and saving energy, but also relax capacity. The only thing is that the relief capacity is not exerted and the real capacity is not improved. However, if adjusting process conditions on $1^{st}$ extractive fractionator and $2^{nd}$ distillation column occurs prior to improving load, it will increase yield, save energy, release output and exert the relaxed capacity to improve real throughput.

The technical proposal of this invention is applicable to CAN process and NMP process of butadiene extraction unit as well.

The invention claimed is:

1. A process of butadiene-1,3 extraction, comprising:
feeding a C4 material to a middle portion of a first extractive fractionator, a solvent to a top portion of the first extractive fractionator; wherein, by extractive fractionating, butane and butylene is separated from the top of a column of the first extractive fractionator, butadiene-1,3, trans-butylene-2, cis-butylene-2, butadiene-1,2, butyne-1, vinyl acetylene and solvent are discharged from the bottom to a first stripper and, after separation, butadiene-1,3, trans-butylene-2, cis-butylene-2, butadiene-1,2, butyne-1, vinyl acetylene get out from the top of the first stripper and solvent is discharged from the bottom of the first stripper;
pressuring butadiene-1,3, trans-butylene-2, cis-butylene-2, butadiene-1,2, butyne-1, vinyl acetylene discharged from the top of the first stripper, and sending them to the bottom of a second extractive fractionator, and further introducing a solvent from the top of the second extractive fractionator; wherein, by extractive fractionation, crude butadiene comes out from the top of the second extractive fractionator and liquid in the column of the second extractive fractionator is discharged from the bottom of the second extractive fractionator to a butadiene recovery column and, after separation, butadiene-1,3 discharged from the top of the butadiene recovery column is fed to a compressor and liquid in the column gets out from the bottom of the butadiene recovery column to a second stripper, vinyl acetylene offgas is discharged from the top of the second stripper after separation and solvent comes out from the bottom of the column;
introducing the crude butadiene from the second extractive fractionator to the top of a first distillation column; wherein, by separation, methyl acetylene offgas is discharged from the top of the first distillation column, the mixture at bottom is sent to the upper portion of a second distillation column for separation and, then, butadiene-1,3 is drawn from the top of the second distillation column and bottom waste containing $C_4$ and $C_5$ is discharged to a vaporizer to remove inhibitor, and then enters to the top of the second stripper for diluting vinyl acetylene offgas;
partially introducing the butane and butylene separated by the first extractive fractionator to the top of a alkyne fractionator, introducing the vinyl acetylene offgas separated by the second stripper to the bottom of the alkyne fractionator, and introducing the methyl acetylene offgas from the first distillation column to the top of the alkyne fractionator; wherein, by re-separating, butadiene-1,3 is side-drawn from the middle of the alkyne fractionator and returns to the first extractive fractionator through a feed vaporizer, methyl acetylene is vent from the top of the alkyne fractionator and vinyl acetylene is discharged from the bottom of the alkyne fractionator.

2. According to the butadiene-1,3 extraction process described in claim 1, wherein, by decreasing solvent ratio and reflux ratio of the first extractive fractionator, the trans-butylene-2 separated from the bottom of the first extractive fractionator is 0.1-0.15% and cis-butylene-2 is 3.0-3.5%; by increasing waste $C_4$ and $C_5$ discharge of the second distillation column bottom, 10-15% of butadiene-1,3 in the second distillation column bottom can be obtained.

* * * * *